(12) United States Patent
Cani et al.

(10) Patent No.: US 11,744,784 B2
(45) Date of Patent: Sep. 5, 2023

(54) DYED PARTICLES WITH A HIGH PIGMENT CONTENT

(71) Applicant: CAPSUM, Marseilles (FR)

(72) Inventors: Julie Cani, Aubagne (FR); Cassia Michel, Marseilles (FR); Morgane Forest, Marseilles (FR)

(73) Assignee: CAPSUM, Marseilles (FR)

( * ) Notice: Subject to any disclaimer, the term of this patent is extended or adjusted under 35 U.S.C. 154(b) by 209 days.

(21) Appl. No.: 16/498,416

(22) PCT Filed: Mar. 30, 2018

(86) PCT No.: PCT/EP2018/058331
§ 371 (c)(1),
(2) Date: Sep. 27, 2019

(87) PCT Pub. No.: WO2018/178353
PCT Pub. Date: Oct. 4, 2018

(65) Prior Publication Data
US 2020/0188242 A1    Jun. 18, 2020

(30) Foreign Application Priority Data
Mar. 30, 2017    (FR) .................................... 17 52731

(51) Int. Cl.
| | | |
|---|---|---|
| *A61K 8/11* | (2006.01) | |
| *A61K 8/02* | (2006.01) | |
| *A61K 8/20* | (2006.01) | |
| *A61K 8/29* | (2006.01) | |
| *A61K 8/34* | (2006.01) | |
| *A61K 8/55* | (2006.01) | |
| *A61K 8/73* | (2006.01) | |
| *A61Q 1/02* | (2006.01) | |
| *A61Q 5/00* | (2006.01) | |

(52) U.S. Cl.
CPC .............. *A61K 8/11* (2013.01); *A61K 8/0216* (2013.01); *A61K 8/20* (2013.01); *A61K 8/29* (2013.01); *A61K 8/345* (2013.01); *A61K 8/55* (2013.01); *A61K 8/73* (2013.01); *A61Q 1/02* (2013.01); *A61Q 5/00* (2013.01); *A61K 2800/412* (2013.01); *A61K 2800/43* (2013.01); *A61K 2800/621* (2013.01); *A61K 2800/622* (2013.01); *A61K 2800/651* (2013.01); *A61K 2800/652* (2013.01)

(58) Field of Classification Search
CPC .......... A61K 8/11; A61K 8/0216; A61K 8/20; A61K 8/29; A61K 8/345; A61K 8/55; A61K 8/73; A61K 2800/412; A61K 2800/43; A61K 2800/621; A61K 2800/622; A61K 2800/651; A61K 2800/652; A61K 8/19; A61Q 1/02; A61Q 5/00

See application file for complete search history.

(56) References Cited

U.S. PATENT DOCUMENTS

| | | | | |
|---|---|---|---|---|
| 3,919,110 | A | * | 11/1975 | Vassiliades ............ B01J 13/203 521/64 |
| 9,707,161 | B2 | | 7/2017 | Liu et al. |
| 2012/0315312 | A1 | * | 12/2012 | Riedemann ............... A61K 8/11 424/401 |
| 2015/0272840 | A1 | | 10/2015 | Liu et al. |

FOREIGN PATENT DOCUMENTS

| | | | | |
|---|---|---|---|---|
| CN | 104812359 A | | 7/2015 | |
| EP | 1 036 555 A1 | | 9/2000 | |
| EP | 1 413 298 A1 | | 4/2004 | |
| FR | 2 827 161 A1 | | 1/2003 | |
| FR | 2 969 907 A1 | | 7/2012 | |
| FR | 2 973 225 A1 | | 10/2012 | |
| FR | 3 031 306 A1 | | 7/2016 | |
| WO | WO 00/78280 A1 | | 12/2000 | |
| WO | WO-2011006657 A1 * | | 1/2011 | ............ A61Q 19/10 |
| WO | WO 2012/089820 A1 | | 7/2012 | |
| WO | WO 2012/120098 A2 | | 9/2012 | |
| WO | WO-2014062689 A1 * | | 4/2014 | ........... A61K 8/0241 |
| WO | WO-2014082299 A1 * | | 6/2014 | ............... A61K 8/92 |

OTHER PUBLICATIONS

Viladot Petit et al. (EP1413298A1 Machine Translation) (Year: 2004).*
Pahlck et al. (WO1991006277A1) (Year: 1991).*
International Search Report dated May 30, 2018 in International Application No. PCT/EP2018/058331.
Written Opinion in International Application No. PCT/EP2018/058331.
Preliminary Search Report in French Patent Application No. FR 17 52731.

* cited by examiner

Primary Examiner — Robert A Wax
Assistant Examiner — Quanglong N Truong
(74) Attorney, Agent, or Firm — Pearne & Gordon LLP

(57) ABSTRACT

A series of particles, in which each particle contains at least 3 wt. % of pigment(s) in relation to the weight of the particle, a method for producing the series of particles, and uses thereof in cosmetic compositions, particularly in make-up for keratinous materials.

14 Claims, No Drawings

DYED PARTICLES WITH A HIGH PIGMENT CONTENT

The present invention relates to colored particles with a high pigment content intended to be incorporated into cosmetic compositions, in particular make-up compositions and to a method for preparation thereof.

Within the meaning of the present invention, the term "cosmetic composition" is understood to refer to any cosmetic formulation intended to be applied to the skin, the hair and/or the nails.

One of the main objectives in the cosmetics field is to improve the external appearance of the skin, in particular the face. Generally, make-up foundations are used to enhance facial features or mask perceived skin imperfections. These make-up foundations are generally available in the form of liquid, semi-liquid or cream suspensions, emulsions, gels, as well as pressed powders or anhydrous oils and wax compositions.

There is a need to develop new cosmetic compositions that offer novel sensorially appealing experiences to the user and/or that are more effective. In recent years formulations have been developed in the form of macroscopic particles, in particular of the bead type, whether hollow or solid, flexible or rigid. These macroscopic particles confer a highly differentiating and very attractive visual appearance, while also protecting the encapsulated active ingredients and agents therein. Be that as it may, existing macroscopic particles however, are generally either not at all or very slightly colored, and are used in skincare products that are only mildly if at all colored, or whose ability and capacity to color keratinous materials is/are largely insufficient.

Some colored macroscopic particles comprising dyes (chemical coloring substance that is soluble in the colored/dyed particle) have previously been disclosed. However, their dye content levels are very low. Few macroscopic colored particles comprising a pigment (powdery and insoluble chemical coloring substance) are known, and their pigment content levels are extremely low, which serves to make them unsuitable for use as a make-up composition constituents. In addition, these low content levels of pigments are such that the corresponding cosmetic products have properties in terms of coverage that are not entirely satisfactory.

Because of their pulverulent or powdery and insoluble nature, the pigments are indeed difficult to integrate within the macroscopic particles. In fact, particle preparation methods for preparing macroscopic particle generally make use of solutions in implementation. However, introducing pigments into these solutions generally makes them very viscous, and the usual methods of preparation are then very difficult to implement. In addition, in the rare cases where it is possible to formulate a colored macroscopic particle comprising a pigment, it is observed that a phenomenon of sedimentation of the pigment within the interior of the colored macroscopic particle occurs. Therefore, it is sought to obtain colored macroscopic particles in which the pigment is well distributed throughout the entire macroscopic colored particle (or throughout the entire phase within which it is contained, where the macroscopic particle is multiphasic and the pigment is in one phase).

The development of macroscopic particles with high levels of pigment content and not presenting the above-mentioned disadvantages for cosmetics applications, in particular related to make-up, thus remains an ongoing objective.

In particular, the present invention serves the object of providing a cosmetic composition comprising macroscopic particles and possessing satisfactory properties in terms of coverage.

To this end, the invention relates to a particle, in particular a macroscopic particle, that comprises at least 3% by weight of pigment(s), generally at least 5% by weight of pigment(s), in particular at least 10% by weight of pigment(s), typically at least 13% by weight of pigment(s), in relation to the weight of the said particle.

The particles of the invention may comprise up to 50% by weight of pigment(s). When a plurality of pigments are present, this weight proportion is the cumulative proportion of the pigments. These proportions are expressed in relation to the weight of the particles. The particles according to the invention may in particular be referred to as "colored particles" or "colored macroscopic particles". The particles according to the invention therefore comprise at least one pigment but are different from the pigments. In fact, they comprise, in addition to pigments, other constituents, as explained in particular here below. According to the invention, the pigments are one of the constituents of the particles of the invention but they are not the only constituents of the said particles. The particles according to the invention are therefore elements that are different (or distinct) from the pigment(s) as such.

The invention also relates to a series of particles as defined here above.

The invention also relates to a composition comprising at least one particle as defined here above or at least one series of particles as defined here above.

The colored particles according to the invention have a substantially spherical shaped form.

The particles according to the invention are advantageously macroscopic, that is to say visible to the naked eye.

Their mean diameters D are generally in a range from 0.1 mm to 10 mm, in particular from 0.1 to 7 mm, preferably from 0.2 mm to 5 mm, typically from 0.3 mm to 3 mm, in particular from 0.4 mm to 2.5 mm, for example from 0.5 mm to 2 mm. This diameter is advantageously measured on N colored particles by means of the image processing software "Image J", on the basis of a snapshot of the colored particles taken from a top view perspective with a digital camera device. Typically, according to this method, the diameter is measured in pixels, and then reported in µm, as a function of the size of the container containing the colored particles. Preferably, the value of N is chosen so as to be greater than or equal to 30, in a manner such that this analysis reflects in a statistically significant manner the distribution of diameters of the colored particles.

The diameter $D_i$ of each colored particle is measured, then the mean diameter is obtained by calculating the arithmetic mean of these values $D_i$:

$$\overline{D} = \frac{1}{N} \sum_{i=1}^{N} D_i$$

Based on these values $D_i$, it is also possible to obtain the standard deviation of the diameters of the colored particles:

$$\sigma = \sqrt{\frac{\sum_{i=1}^{N} (D_i - \overline{D})^2}{N}}$$

The standard deviation σ reflects the distribution of the diameters $D_i$ of the colored particles around the mean diameter $\overline{D}$.

The coefficient of variation $C_v$ can be calculated as follows:

$$C_v = \frac{\sigma}{\overline{D}}$$

This parameter reflects the distribution of the diameters of the colored particles as a function of the mean diameter of these particles.

According to one embodiment, in the series of particles according to the invention, the coefficient of variation of the diameters of the colored particles is less than 10%, preferably less than 5%.

According to one embodiment, in the aforementioned composition, the coefficient of variation of the diameters of the colored particles is less than 10%, preferably less than 5%.

The colored particles can be monophasic or multiphasic. For example, they comprise a core (which is comprised of at least one phase) and an enveloping shell or membrane (which constitutes another phase) that completely encapsulates the core. The core is preferably liquid at 25° C. The core itself may include one or more phases. Generally, the at least one pigment is present in the phase (one of the phases) that forms the core. The enveloping shell that completely encapsulates the core is typically constituted based on at least one gelled polyelectrolyte and/or at least one polymer, that is preferably temperature-sensitive, for example agar-agar. Each phase of the colored particles may be oily or aqueous.

According to one embodiment, a particle according to the invention is a solid (or monophasic) particle. Among these particles, mention may be made in particular of particles constituted based on at least one gelled polyelectrolyte and/or at least one polymer, that is preferably temperature-sensitive, for example agar-agar. Preferably, mention may be made of agar beads and particles formed from one single phase corresponding to the aforementioned gelled polyelectrolyte.

According to another embodiment, a particle according to the invention is a particle of the core/shell (as per the accepted terminology) type, also referred to by the term "capsule".

According to one embodiment, a particle according to the invention is a capsule that comprises a core that is liquid, or at least partially gelled or at least partially thixotropic, and an enveloping shell, preferably gelled, which totally encapsulates the said liquid core, the said liquid core being monophasic, and in particular constituted based on a predominantly aqueous phase or on the contrary, a predominantly oily phase. Advantageously, the enveloping shell is constituted based on at least one gelled polyelectrolyte and/or at least one polymer, that is preferably temperature-sensitive, for example agar-agar.

Such a type of particle thus then corresponds to a simple capsule comprising two distinct phases, an internal phase that is liquid, or at least partially gelled or at least partially thixotropic, and an external phase in the solid or gelled state that surrounds the internal phase.

According to one particular embodiment, a particle according to the invention is a capsule which comprises a core that is liquid, or at least partially gelled or at least partially thixotropic, and an enveloping shell, preferably gelled, that totally encapsulates the said core, the said core comprising an intermediate droplet of an intermediate phase, the intermediate phase being placed in contact with the enveloping shell, and at least one, preferably one single, internal droplet of an internal phase being disposed in the intermediate droplet. Here again, advantageously, the enveloping shell is constituted based on at least one gelled polyelectrolyte and/or at least one polymer, that is preferably temperature-sensitive, for example agar-agar. Advantageously, the ratio of the volume of the core to the volume of the gelled enveloping shell is greater than 2, advantageously less than 50, and preferably is comprised between 5 and 10. The intermediate phase is for example constituted based on an aqueous or oily solution. When the intermediate phase is aqueous, the internal phase is oily, and conversely when the intermediate phase is oily, the internal phase is aqueous.

Such a type of particle then corresponds to a complex capsule signifying that the core, being liquid, viscous or thixotropic, comprises one single intermediate droplet of an intermediate phase, the intermediate phase being placed in contact with the enveloping shell, and at least one, preferably one single, internal droplet of an internal phase being disposed in the intermediate droplet.

According to one variant, the core comprises a continuous intermediate phase within which are found a plurality of droplets(s) of the internal phase(s).

According to one embodiment, a particle according to the invention comprises a core that is liquid, or at least partially gelled or at least partially thixotropic and an enveloping shell, preferably gelled, that completely encapsulates the said core, the said core comprising an intermediate droplet of an oily phase, the oily phase being placed in contact with the enveloping shell, and at least one internal droplet of an aqueous phase being disposed in the intermediate droplet.

According to another embodiment, a particle according to the invention comprises a core that is liquid, or at least partially gelled or at least partially thixotropic and an enveloping shell, preferably gelled, that completely encapsulates the said core, the said core comprising an intermediate droplet of an aqueous phase, the aqueous phase being placed in contact with the enveloping shell, and at least one, preferably one single, internal droplet of an oily phase being disposed in the intermediate droplet.

Advantageously, the intermediate phase in addition comprises at least one gelling agent, in particular as defined here below. In particular, the gelling agent contributes to improving the suspension of the one or more internal droplet(s) disposed in the intermediate droplet of the particles of the invention according to this embodiment. In other words, the gelling agent makes it possible to prevent/avoid the phenomena of creaming or sedimentation of the one or more internal droplet(s) disposed in the intermediate droplet of the particles of the invention according to this embodiment.

The colored particles comprise at least one pigment, preferably a plurality of pigments. The use of a plurality of pigments makes it possible to more finely adjust the coloring of the colored particles obtained as desired.

The term "pigment" is understood to refer to a chemical coloring substance that is insoluble in the colored particle (or the phase of the colored particle in which the pigment is present). The term "insoluble" is understood to indicate that the solubility at 20° C. of the pigment in the colored particle (or the phase of the colored particle in which the pigment is present) is less than 1 g/L, in particular less than 0.1 g/L, preferably less than 0.001 g/L.

Each pigment may independently be an organic, inorganic or hybrid organic-inorganic pigment. The invention typically involves inorganic pigments.

With respect to pigments, in particular mention may be made of titanium dioxide, zinc dioxide, zirconium or cerium oxides, as well as iron or chromium oxides, manganese violet, ultramarine blue, chromium hydrate and ferric blue, and the mixtures thereof. The preferred inorganic pigments are iron oxides, in particular red iron oxide, yellow iron oxide, brown iron oxide, black iron oxide, titanium dioxide and mixtures thereof.

The pigment is preferably an iron oxide, in particular red iron oxide, yellow iron oxide, brown iron oxide, black iron oxide and mixtures thereof.

Each pigment of the colored particles may be an untreated pigment or a treated pigment. Within the meaning of the present invention, the term "treated pigment" is understood to refer to a pigment which has been treated with an additive thereby improving its dispersibility in an oily or aqueous composition, in particular one of the additives defined here below. The term "untreated pigment" or "not/non treated pigment" is understood to refer to a pigment which has not been treated with such an additive.

According to one embodiment, the phase comprising the pigment(s) is an aqueous phase.

According to one embodiment, the phase comprising the pigment(s) is a fatty or oily substance.

Preferably, when the phase comprising pigments is a fatty or oily phase, the said phase additionally also comprises hydrostearic acid, preferably in a content of between 0.5% and 10%, in particular between 3% and 6%, by weight in relation to the total weight of the phase under consideration. The presence of this particular compound is advantageous in that it makes it possible to reduce the viscosity of a pigment/oil (60:40) ground mix, even more so for a phase that is highly loaded with pigments, and thereby to cause it to become fluid and more easily processable, in particular as it involves the fluidic devices as described here below.

The colored particles are generally formed in whole or in part from at least one polymer, in particular at least one polysaccharide, such as an alginate, a gelatin, a pectin, a cellulose or a cellulose derivative, such as carboxymethylcellulose, agar-agar. According to one particular embodiment, the polysaccharide is a polyelectrolyte, a temperature-sensitive polysaccharide, and mixture thereof.

The colored particles may comprise at least one gelling agent, in particular a temperature-sensitive agent. This gelling agent makes it possible in particular to appropriately adjust the viscosity and/or to reduce or even prevent the sedimentation of the one or more pigment(s), in particular when present in a liquid phase at ambient temperature and atmospheric pressure.

In the context of the invention, the term "gelling agent" is understood to mean an agent which makes it possible, at ambient temperature at atmospheric pressure, to increase the viscosity of the phase(s) in which it is contained as compared to the same phase(s) without the said gelling agent, and in particular enables the phase(s) to attain a final viscosity greater than 20,000 mPa·s, preferably greater than 50,000 mPa·s, better still in excess of 100,000 mPa·s, and most preferably greater than 200,000 mPa·s.

Preferably, the viscosity of the one or more phase(s) that form the colored particles in the presence of the said gelling agent is comprised between 20,000 and 100,000,000 mPa·s, preferably between 50,000 and 1,000,000 mPa·s, and better still between 100,000 and 500,000 mPa·s at 25° C.

The selection of gelling agent(s) is carried out in particular with regard to the nature of the phase and is different from the polysaccharide that forms all or part of the colored particles according to the invention. Thus, for compatibility related reasons:
the gelling agent is hydrophilic when present in an aqueous phase, and
the gelling agent is lipophilic when present in an oily phase.

The term "hydrophilic gelling agent" within the meaning of the present invention, is understood to refer to a compound capable of gelling the aqueous phase of the colored particles. The gelling agent may be water-soluble or water-dispersible. The hydrophilic gelling agent may be selected from among semi-synthetic polymeric gelling agents, synthetic polymeric gelling agents, natural or naturally-sourced polymeric gelling agents, mixed silicates and fumed or pyrogenic silicas, and mixtures thereof. These hydrophilic gelling agents may be cationic, anionic, amphoteric or non-ionic.

The term "lipophilic gelling agent" is understood to refer to a compound that is capable of gelling the oily phase of the colored particles. The gelling agent is liposoluble or lipodispersible. The lipophilic gelling agent is advantageously selected from among particulate gelling agents; organopolysiloxane elastomers; semi-crystalline polymers; polyacrylates; sugar/polysaccharide esters, in particular dextrin esters, inulin esters, glycerol esters, in particular dextrin esters; hydrogen-bonded polymers; hydrocarbon block copolymers and the mixtures thereof.

The hydrophilic or lipophilic gelling agents may be selected from among the agents described in the documents FR 3 025 096 or FR 3 025 103.

The colored particles may in addition comprise a smoothening-concealing effect filler.

A smoothening-concealing effect filler is capable of altering and/or concealing and masking wrinkles by virtue its intrinsic physical properties. These fillers in particular are able to alter wrinkles by means of a tightening effect, a camouflage effect, or a blurring effect.

By way of smoothening-concealing effect fillers, mention may be made of the following compounds as examples:
porous silica microparticles, such as for example the Silica Beads® SB 150 and SB 700 with a mean size of 5 μm, from Myochi, and the SUNSPHERES® H series for example H33, H51, respectively measuring 3.5 μm and 5 μm in size, from Asahi Glass, and Sensibead Si 175 and Sensibead Si 320, respectively measuring 7 μm and 5 μm in size, from Sensient Cosmetic Technologies;
hollow hemispherical particles of silicone resins, such as NLK 500®, NLK 506® and NLK 510® from Takemoto Oil and Fat, in particular described in EP 1 579 849;
silicone resin powders, such as for example SILICON Resin Tospearl® 145 A of GE silicone having a mean size of 4.5 μm;
powders of acrylic copolymers, in particular of methyl poly (meth) acrylate, such as for example the PMMA Jurimer MBI® particles, with a mean size of 8 μm, from Nihon Junyoki, and the hollow spheres of PMMA sold under the trade name/reference COVABEAD® LH 85 by the company Sensient Cosmetic Technologies, and the expanded microspheres of vinylidene/acrylonitrile/methylene methacrylates sold under the trade name/reference Expancel®;

wax powders such as the Paraffin wax Microloase® 114S particles with a mean size of 7 μm, from Micropowders;

polyethylene powders, in particular comprising at least one ethylene/acrylic acid copolymer, for example the FLOBEADS® EA 209 E with a mean size of 10 μm, from Sumimoto;

crosslinked elastomeric organopolysiloxane powders coated with silicone resin, in particular with silsesquioxane, made available under the trade name/reference KSP 100®, KSP 101®, KSP 102®, KSP 103®, KSP 104® and KSP 105® by the company Shin Etsu;

composite powders of talc/dioxide or titanium/alumina/silica, such as for example Coverleaf AR 80® from the company Catalyst & Chemical;

talc, mica, kaolin, lauryl glycine, starch powders crosslinked with octenyl succinic anhydride [anhydride octéanyl succinate], boron nitride, polytetrafluoroethylene powders, precipitated calcium carbonate, magnesium hydrocarbonate carbonate, barium sulfate, hydroxyapatite, calcium silicate, cerium dioxide and microcapsules of glass or ceramics;

synthetic or natural hydrophilic or hydrophobic fibres, whether inorganic/mineral or organic, such as fibres of silk, cotton, wool, flax, cellulose extracted in particular from wood, vegetables or algae, fibres of polyamide (Nylon®), modified cellulose, poly-p-phenylene terephtamide, acrylic, polyolefin, glass, silica, aramid, carbon, polytetrafluoroethylene (Teflon®), insoluble collagen, polyesters, polyvinyl chloride or polyvinylidene chloride, polyvinyl alcohol, polyacrylonitrile, chitosan, polyurethane, polyethylene phthalate, fibres formed from a mixture of polymers, synthetic resorbable fibres, and the mixtures thereof as described in the patent application EP 1 151 742;

spherical elastomeric crosslinked silicones such as for example Trefil E-505C® or E-506 C® from Dow Corning;

abrasive fillers which, by means of a mechanical effect, provide a smoothing of the cutaneous microrelief, such as abrasive silica, like for example Abrasif SP® from Semanez, or powders of walnut or shells (apricot, walnut, for example from Cosmetochem).

The fillers that have an effect on the visible signs of aging are chosen in particular from among porous silica microparticles, hollow hemispherical silicone particles, silicone resin powders, acrylic copolymer powders, polyethylene powders, and crosslinked elastomeric organopolysiloxane powders coated with silicone resin, composite powders of talc/dioxide and titanium/alumina/silica, precipitated calcium carbonate, magnesium hydrocarbonate and magnesium carbonate, barium sulfate, hydroxyapatite, calcium silicate, cerium dioxide and microcapsules of glass or ceramics, silk fibres, cotton fibres, and mixtures thereof.

The colored particles may in addition comprise a "soft focus" filler. The term "soft-focus" filler, is understood to refer to a filler which in addition provides an effect of transparency to the complexion along with a defocused blurry effect.

Preferably, the "soft-focus" fillers have an mean particle size of less than or equal to 15 microns. These particles may be of any shape and in particular be spherical or non-spherical. More preferably, these fillers are non-spherical.

The "soft-focus" fillers may be selected from among silica and silicate powders, in particular alumina powders, polymethyl methacrylate (PMMA) type powders, talc, composites of silica/$TiO_2$ or silica/zinc oxide, polyethylene powders, starch powders, polyamide powders, powders of styrene/acrylic copolymers, silicone elastomers, and the mixtures thereof.

In particular, mention may be made of talc with a number mean particle size that is less than or equal to 3 microns, for example talc with a number mean particle size of 1.8 microns, and in particular the one sold under the trade name Talc P3® by the company Nippon Talc, Nylon® 12 powder, in particular that sold under the trade name/reference Orgasol 2002 Extra D Nat Cos® by the company Atochem, silica particles treated on the surface with a mineral wax 1 to 2% (INCI name: hydrated silica (and) paraffin) such as those marketed by the company Degussa, amorphous silica microspheres, such as those sold under the trade name/reference Sunsphere, for example under the reference H-53® by the company Asahi Glass, silica micro-beads such as those sold under under the trade name/reference SB-700® or SB-150® by the company Miyoshi, Sensibead Si 175 and Sensibead Si 320 silica beads from Sensient Cosmetic Technologies, and the beads PMMA Covabead Velvet 10 and Covabead Velvet 20 from the company Sensient, this list by no means being exhaustive.

Given the effect they have on the signs of aging, the concentration of these fillers in the colored particles may be comprised between 0.1% and 60%, or indeed even between 0.5% and 40%, in particular between 1% and 20%, by weight in relation to the total weight of the colored particles.

According to one embodiment, a colored particle according to the invention in addition comprises at least one colouring agent that is different from the above-mentioned pigment(s).

The colored particles may therefore also comprise a dye and/or a pearlescent pigment (nacre), for example a nacre 2375 Gold Covapearl Star nacre from Sensient Cosmetic Technologies or Covapearl Antique Silver 239 from Sensient Cosmetic Technologies. Preferably, a dye or a pearlescent pigment of a different colour from that of the pigment used will be chosen. The term "dye" is understood to refer to a chemical colouring substance that is soluble in the colored particle (or the phase of the colored particle in which the dye is present). The term "soluble" is understood to indicate that the solubility at 20° C. of the dye in the colored particle is greater than 2 g/l, in particular greater than 5 g/l, preferably greater than 10 g/l.

Preferably, when the colored particles are multiphasic particles, the phase comprising the pigment(s) is different from the phase comprising the pearlescent pigment(s) or the dye(s). This consequently results in a visual effect that is heightened, and even unexpected, for the consumer who, according to one particular embodiment, sees emerging out of the container a cosmetic composition of a color (that of the pearlescent pigment(s) and/or dye(s)) that is totally different from the color expected (that of the pigment of the colored particles).

According to one embodiment, when the particle according to the invention is a simple capsule as defined here above, the core comprises at least 3%, in particular at least 5%, by weight of pigments, and the membrane comprises at least one coloring agent, in particular pearlescent pigments, of a color different from that of the encapsulated pigments (and therefore of the core), preferably in a content level such that the membrane (or enveloping shell) prevents the content of the capsule from being visible. This accordingly results in an unexpected effect for the consumer who sees emerging out of the pack a composition of a color that is completely different from the color of the capsules.

According to one embodiment, when the particle according to the invention is a complex capsule as defined here above, the core comprises at least 3%, in particular at least 5%, by weight of pigments, and, according to a first variant the pigments are present in the internal phase (IF), the intermediate phase (MF), or both, and according to a second variant, the membrane comprises at least one coloring agent, in particular pearlescent pigments, preferably of a color different from that of the encapsulated pigments (and therefore of the core), preferably in a content level such that the membrane (or enveloping shell) prevents the content of the capsule from being visible. This accordingly results in unexpected visual effects for the consumer who sees emerging out of the pack a composition of a color that is completely different from the color of the capsules.

The particles according to the invention may in addition comprise at least one additional compound different from the abovementioned compounds.

A particle according to the invention, in particular the core and/or the enveloping shell of a capsule according to the invention, may thus in addition comprise, by way of an additional compound, powders, flakes, particulate agents that are insoluble in the fatty phase, emulsifying and/or non-emulsifying silicone elastomers, in particular as described in the patent application EP 2 353 577, preservatives, humectants, stabilizers, chelators, emollients, modifying agents selected from among pH agents, osmotic force agents and/or refractive index modifiers etc, or any usual cosmetic additive, and the mixtures thereof.

A particle according to the invention, in particular the core and/or the enveloping shell of a capsule according to the invention, may in addition comprise at least one active agent, in particular a biological or a cosmetic active agent, preferably selected from among hydrating agents, healing agents, depigmenting agents, UV filters, desquamating agents, antioxidant agents, active agents that stimulate dermal and/or epidermal macromolecular synthesis, dermo-decontracting agents, antiperspirant agents, soothing agents, anti-aging agents, perfuming agents and the mixtures thereof. Such active ingredients and agents are in particular described in the patent application FR 1 558 849.

Obviously, the person skilled in the art will exercise care in selecting the possible optional additional compound(s) and/or active agent(s) mentioned above and/or the respective quantities thereof in a manner so as to ensure that the advantageous properties of the particles according to the invention are either not at all or not substantially altered or impaired by the envisaged addition. These adjustments fall within the expertise and general knowledge of the person skilled in the art.

The invention also relates to a particle preparation method for preparing a series of colored particles comprising a pigment formulation step c) for formulating at least one pigment in the form of a series of colored particles comprising at least 3% by weight of pigment.

According to a first alternative of the method, the pigment used in implementation in the step c) is an untreated and unmilled pigment (pigment used "as is").

According to a second alternative of the method, the pigment used in implementation in the step c) has been subjected to an initial pre-treatment in order to make it more easily dispersible during the formulation of the pigment. This initial pretreatment consists in grinding the pigment and/or in pretreating it with an additive that improves its dispersibility prior to formulating it in the form of a series of colored particles.

The preparation method then comprises the steps consisting of:

a) providing at least one pigment that is optionally pretreated with an additive that improves the dispersibility of the pigment, then b) optionally grinding the said at least one pigment, the said grinding preferably taking place when the at least one a pigment is not pretreated, c) formulating the at least one pigment obtained in the step a) or b) in the form of a series of colored particles comprising at least 3% by weight of pigment(s).

The invention is based in particular on the discovery that the use of a ground pigment and/or a pigment pretreated with an additive that improves its dispersibility:

contributes to ensuring that a liquid which contains the milled and/or pretreated pigment has a low viscosity;

contributes to the preparation of colored particles having a very high content of pigment(s), comprising more than 3% by weight of pigment(s), generally more than 5% by weight of pigment(s), or indeed even more than 7.5% by weight of pigment(s)

contributes to the reduction of, or indeed even prevents, the sedimentation of the pigment(s) in the phase(s) of the colored particles that contain(s) it(them), and/or contributes to the reduction of, or indeed even prevents, aggregation of the pigments in the phase(s) of the colored particles that contain(s) it(them).

Generally, when a plurality of pigments are used, they are all subjected to the same treatment, that is to say they are all ground and/or they are all pretreated. It is possible, however, for some to be ground and untreated, and for others to be treated and ground or unmilled.

According to a first embodiment of the method according to the second alternative, the at least one pigment of the step a) is pretreated with an additive that improves the dispersibility of the pigment.

The nature of the additive that improves the dispersibility of the pigment depends on the hydrophilic or lipophilic nature of the phase(s) of the colored particle which will contain this treated pigment.

When the method makes use in implementation of a plurality of pretreated pigments, these latter may be pretreated with additives that are identical or different from one another.

An additive that improves the dispersibility of the pigment within an oily composition is selected in order to prepare the colored particles whereof the phase(s) that will contain the pigment is oily. The additive is for example selected from among hydrogenated lecithin, a silicone, a wax, an amino acid or one of the salts thereof and an amino acid ester or one of the salts thereof. Hydrogenated lecithin comprises phosphate mono- and di-ester having fatty chains which promote dispersibility in the oily phase. The silicone additive may either be obtained from a silicone precursor, such as an alkoxyalkylsilane like triethoxycaprylsilane, or such as a trialkylsiloxysilicate like trimethylsiloxysilicate; or be a silicone, such as dimethicone or a derivative thereof, for example bis-hydroxyethoxypropyl dimethicone; or be obtained from a mixture of silicone and a precursor thereof, for example a dimethicone and trimethylsiloxysilicate mixture. The silicone additive may be a hybrid treatment, particularly a mixture of isopropyl titanium triisostearate, bis-hydroxyethoxypropyl dimethicone, PEG-2 soyamine and isophorone diisocyanate (IPDI). The wax may for example be pink floral wax. The preferred amino acid is cystine, and the preferred amino acid esters are sodium cocoyl glutamate, lauroyl arginine or lauroyl lysine.

An additive that improves the dispersibility of the pigment within an aqueous composition is selected in order to prepare the colored particles whereof the phase(s) that will contain the pigment is aqueous. This additive in particular is one having the following formula (I):

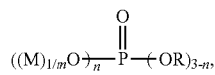
(I)

in which:

n represents 1 or 2,

M represents H or a cation, m represents 1 when M is H and m represents the valence of the cation when M is a cation, R represents:

a G group selected from a saccharide or a group —[CH2-CHR1-O]q-R2 or [CH2-CH (CH2OH)—O]$_q$—R$_2$ in which:

q represents an integer from 1 to 1000, for each unit $CH_2$—$CHR_1$—O, R1 independently represents H or a methyl, R2 represents H or an alkyl comprising from 1 to 3 carbon atoms, and a hydrocarbon chain comprising from 1 to 500 carbon atoms substituted by one or more groups G, phosphate (having the formula $OPO_3(M)_{2/m}$) and/or hydroxyl (OH).

The group —[$CH_2$—$CHR_1$—O]$_q$—$R_2$ with R1 representing H corresponds to a polyethylene glycol (PEG). The group —[$CH_2$—$CHR_1$—O]$_q$—$R_2$ with R1 representing a methyl corresponds to a polypropylene glycol (PPG). The group [$CH_2$—$CH(CH_2OH)$—O]$_q$—R' corresponds to a polyglycerol.

Typically, q is an integer from 1 to 500, in particular from 1 to 100, preferably from 1 to 60.

Preferably, n represents 2 and the additive has the following formula (I'):

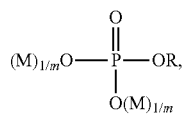
(I')

in which M, m and R are as defined here above.

For the purposes of the present application, a hydrocarbon chain comprises from 1 to 500 carbon atoms, in particular from 1 to 50, typically from 1 to 10 carbon atoms, preferably from 1 to 5 carbon atoms. The hydrocarbon chains may be linear, branched or cyclic. The preferred hydrocarbon chains are alkyl groups (preferably having from 1 to 10 carbon atoms, in particular from 1 to 5 carbon atoms, preferably 1 to 3, such as methyl, ethyl, n-propyl and isopropyl groups), alkenyl groups (preferably having from 2 to 10 carbon atoms, in particular from 2 to 6), aryl groups (preferably having from 6 to 10 carbon atoms), arylalkyl groups (preferably having from 7 to 10 carbon atoms), or alkylaryl groups (preferably having from 7 to 10 carbon atoms). The vinyl group is the preferred alkenyl group. The phenyl group is the preferred aryl.

A saccharide may be a mono- or polysaccharide. The preferred saccharides are mono- or disaccharide, in particular monosaccharides such as glucose, galactose or fructose.

M may in particular be an inorganic cation, such as $Ag^{3+}$, $Al^{3+}$, $Fe^{2+}$, $Fe^{3+}$, $Ag^{2+}$, $Zn^{2+}$, $Sn^{2+}$, $Ca^{2+}$, $Ba^{2+}$, $Ag^+$, $Na^+$ or an organic cation, such as a diethanolammonium (DEA) ($H_3N^+$—$(CH_2)_2$—OH) or a quaternary ammonium.

The following additives having the formula (II), (III) or (IV) are particularly suitable for the operational implementation of the invention:

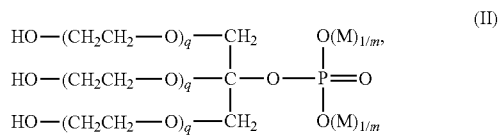
(II)

in which M, m and q are as defined here above, (which corresponds to an additive having the formula (I) in which n represents 2 and R represents an isopropyl hydrocarbon chain, of which each of the carbon atoms is substituted by a group G which represents —[$CH_2$—$CHR_1$—O]$_q$—$R_2$ where $R_1$ and $R_2$ represent H),

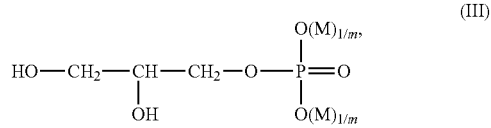
(III)

in which M and m are as defined here above, (which corresponds to an additive having the formula (I) in which n represents 2, R represents a group G having the formula —[$CH_2$—$CH(CH_2OH)$—O]$_q$—$R_2$ where q represents 1 and $R_2$ represents H),

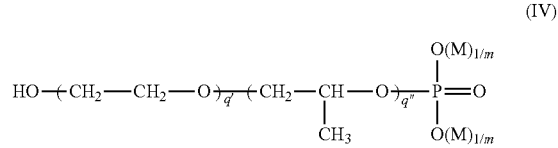
(IV)

in which M and m are as defined here above and q' and q" independently represent an integer from 0 to 1000, generally from 0 to 500, in particular from 0 to 100, preferably from 0 to 60, such that the sum of q' and q" independently represent an integer from 1 to 1000, (which corresponds to an additive having the formula (I) in which n represents 2, R represents a group G having the formula —[$CH_2$—$CHR_1$—O]$_q$—$R_2$ where q represents the sum of q' and q" and, for the q" first units, $R_1$ represents a methyl and for the q' last units, $R_1$ represents H, and $R_2$ represents H).

The following additives having the formulas (V) and (VI) are also suitable:

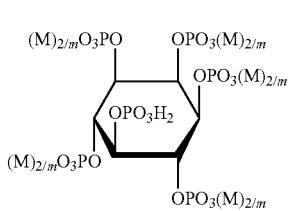

(which corresponds to an additive having the formula (I) in which n represents 2, R represents a cyclohexyl hydrocarbon chain substituted at the positions 2, 3, 4, 5 and 6 by a phosphate group having the formula $OPO_3H_2$),

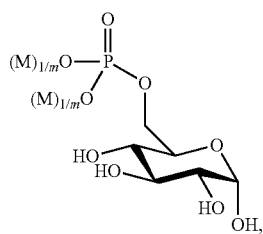

(which corresponds to an additive having the formula (I) in which n represents 2, R represents a methyl hydrocarbon chain linked to a group G glucose), in which M and m are as defined here above.

The following additives are particularly preferred:

the glycereth-26 phosphate having the formula (II') below:

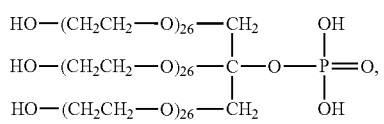

(which corresponds to an additive having the formula (II) in which M represents H and m represents 1), this additive being advantageously available in the commercial channel, for example from Croda®, glycerophosphate having the formula (III') below:

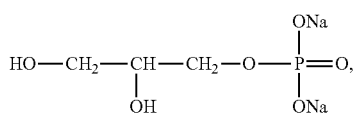

(which corresponds to an additive having the formula (III) in which M represents Na and m represents 1), this additive being advantageously available in the commercial channels, for example from Dr. Paul Lohman®, the phosphate PEG-26 and PPG-30 of diethanolammonium having the formula (IV') below:

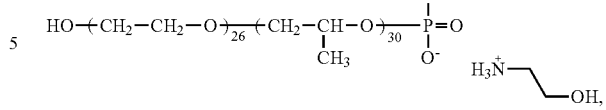

(which corresponds to an additive having the formula (IV) in which M represents a diethanolammonium cation and m represents 1), the said additive being advantageously available in the commercial channel, for example from Innospec®, phytic acid having the formula (VI') below:

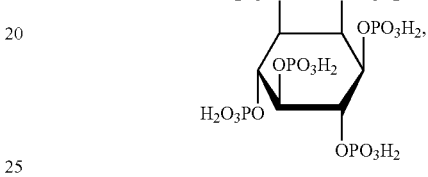

(which corresponds to an additive having the formula (V) in which M represents H and m represents 1), the said additive being advantageously available in the commercial channel, for example from NutriScience®, glucose phosphate having the formula (VI') below:

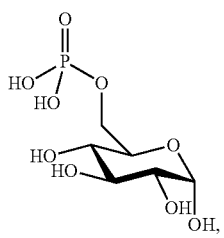

(which corresponds to an additive having the formula (VI) in which M represents H and m represents 1), this additive being advantageously available in the commercial channel.

Phytic acid is the additive that improves the dispersibility of the pigment in a preferred aqueous composition.

The method may comprise, prior to the step a), a step a0) of mixing of a pigment with an additive as defined here above in order to obtain a pretreated pigment. For example, the preparation method described in the patent application WO 2012/120098 may be used.

In this first embodiment of the method according to the second alternative that makes use in implementation of a pretreated pigment, the method may comprise a grinding step b) for grinding the pretreated pigment or be exempt therefrom. This grinding makes it possible to limit or indeed even eliminate the aggregates of the pretreated pigments, which facilitates the subsequent incorporation thereof into the phase(s) of the colored particles and/or contributes to reducing the sedimentation of the pigment in the phase(s) of the colored particles in which it is contained.

This grinding step may be carried out in the presence of a binder, or indeed with no binder present (dry milling).

The binder is, for example, glycerine, propanediol, a hydrogenated starch hydrolyzate, octyldodecanol, castor oil, a mineral oil, isononyl isononanoate, dimethicone and cyclomethicone, isododecane. Preferably, when the pigment is not pretreated or when it is treated with an additive that improves the dispersibility thereof in an aqueous composition, the binder is selected from among propanediol, glycerin and a hydrogenated starch hydrolyzate. Preferably, when the pigment is treated with an additive that improves the dispersibility thereof within an oily composition, the binder is selected from among glycerine, octyldodecanol, castor oil, a mineral oil, isononyl isononanoate, dimethicone and cyclomethicone, isododecane.

The mill is then typically selected from three-roll mills, ball mills and plate mills.

When the milling step is carried out in the absence of a binder, the mill may be a pin mill, a jet micronizer, an impact mill, a hammer mill, a knife mill, a ball mill, a vibrating mill or a cryogenic mill.

According to a second embodiment of the method according to the second alternative, the at least one pigment of the step a) is not pretreated with an additive that improves the dispersibility thereof, and the method then comprises a step b) of grinding the pigment. This grinding makes it possible to limit or even eliminate the aggregates of the pretreated pigments, which facilitates the subsequent incorporation thereof into the phase(s) of the colored particles and/or contributes to reducing the sedimentation of the pigment in the phase(s) of the colored particles in which it is contained.

The embodiments described here above for the grinding are indeed certainly applicable (type of mill, absence or presence of binder).

Whatever the alternative and the embodiment of the method being considered, it comprises a step c) consisting of formulating at least one pigment, in the form of a series of colored particles comprising at least 3% by weight of pigment(s).

Preferably, the pigment is the one obtained in the step a) or b). A liquid comprising a pigment that has been ground and/or pretreated as defined here above indeed has a lower viscosity than a liquid comprising a pigment that is unmilled and untreated. A liquid comprising a ground and/or pretreated pigment can therefore indeed be formulated far more easily in the form of a series of colored particles. In addition, the phase that contains the pigment will be less prone to sedimentation of the pigment.

Generally, the colored particles formulated in the step c) comprise in whole or part at least one polysaccharide, and in particular at least one partially or totally gelled polyelectrolyte.

In a first embodiment, the formulation described in the step c) operationally implements a liquid solution which comprises both the one or more pigment(s), preferably obtained in the step a) or b), and
  either a polyelectrolyte,
  or a solution containing a reagent capable of reacting with a polyelectrolyte.

Typically, the step c) according to this first embodiment includes the following sub-steps:
  C1a) mixing of the at least one pigment, preferably obtained in the step a) or b), with a liquid solution containing at least one liquid polyelectrolyte suitable for gelling,
  C1b) introducing, drop by drop, the mixture obtained in the step C1a) into a solution containing a reagent capable of reacting with the polyelectrolyte in order to induce it to pass at least partially from a liquid state to a gelled state;
  C1c) recovery of the colored particles formed.
  or else the step c) comprises the following sub-steps:
  C2a) mixing of the at least one pigment, preferably obtained in the step a) or b), with a solution containing a reagent capable of reacting with a polyelectrolyte,
  C2b) introducing, drop by drop, the mixture obtained in the step C2a) into a liquid solution containing a liquid polyelectrolyte capable of gelling, whereby the polyelectrolyte (in the immediate proximity of the droplets of mixture obtained in the step C2a) passes at least partially from a liquid state to a gelled state;
  C2c) recovery of the colored particles formed.

The polyelectrolyte is preferably a polyelectrolyte reactive with multivalent ions, in particular a polysaccharide reactive with multivalent ions such as an alkali alginate, a gellan, a pectin, a cellulose or a cellulose derivative, such as carboxymethylcellulose, or agar agar. Preferably, it is an alkaline alginate, such as sodium alginate.

The reagent capable of reacting with the polyelectrolyte in order to induce it to pass from a liquid state to a gelled state is typically a solution comprising multivalent ions such as alkaline earth metal ions selected for example from calcium ions, barium ions, magnesium ions.

When the liquid solution used in the step C1a) or C2a) is oily, the pigment used in the step a) is preferably an untreated pigment or a pigment pretreated with an additive that improves the dispersibility thereof within an oily composition.

When the liquid solution used in the step C1a) or C2a) is aqueous, the pigment used in the step a) is preferably an untreated pigment or a pigment pretreated with an additive that improves the dispersibility thereof in an aqueous composition.

The mixture obtained in the step C1a) or C1b) preferably comprises more than 10% by weight, in particular more than 15% by weight, for example between 20 and 50% by weight of pigment(s) (cumulated content levels when there is a plurality of pigments). Such proportions are in effect adjusted so as to ensure that the mass proportion of pigment(s) in the colored particles obtained at the end of the method is greater than 3% by weight, preferably greater than 5% by weight.

The solution used in the step C2a) may in addition comprise at least one thickening agent, for example a polysaccharide such as xanthan.

In the step C1b), the droplets are immersed in the solution containing a reagent capable of reacting with the polyelectrolyte. In the step C2b), the droplets are immersed in the polyelectrolyte solution. The adjustment of the duration of step C1b) or C2b) makes it possible to obtain partially or totally gelled particles. When all of the polyelectrolyte gels, the colored particles formed are "solid particles", also referred to as monophasic particles. When the polyelectrolyte passes only partially from a liquid state to a gelled state, the colored particles comprise a gelled enveloping shell that completely encapsulates the liquid core. This adjustment of the duration of step C1b) or C2b) falls within the expertise and general knowledge of the person skilled in the art.

In a second embodiment, the formulation described in the step c) operationally implements two distinct liquid solutions, one which comprises the pigment, preferably obtained in the step a) or b), and the other which comprises a polyelectrolyte. The colored particles comprise a core and an enveloping shell that completely encapsulates the core. Generally, the at least one pigment is in the phase (one of the phases) forming the core. Advantageously, the pigment(s) do not migrate into the enveloping shell, which serves to keep it(them) from bleeding out of the particles.

The colored particles may comprise a core that is liquid, or at least partially gelled or at least partially thixotropic, containing the pigment(s), preferably obtained in the step a) or b), and a gelled enveloping shell that completely encapsulates the core. This liquid or at least partially gelled or at least partially thixotropic core may be constituted based on a predominantly oily phase. In this case, if a pretreated pigment has been used in implementation of the method, it is a pretreated pigment with an additive that improves the dispersibility of the pigment within an oily composition. This core may be constituted based on a predominantly aqueous phase. In this case, if a pretreated pigment has been used in implementation of the method, it is a pretreated pigment with an additive that improves the dispersibility of the pigment in an aqueous composition.

When the colored particles comprise a core containing the pigment(s), preferably obtained in the step a) or b), and a gelled enveloping shell that completely encapsulates the core, the step c) typically comprises the following sub-steps:

C3a) separated conveying in a double casing envelope (pipe-in-pipe) of a first liquid solution containing the pigment(s), preferably obtained in the step a) or b), and of a second liquid solution containing at least one liquid polyelectrolyte capable of gelling;

C3b) formation, at the outlet of the double casing enveloping, of a series of droplets, each droplet comprising a central kernel formed of first liquid solution, and a peripheral film formed of second solution and completely covering the central kernel, where the second solution (40) contains at least one surfactant prior to its contact with the first solution;

C3c) detaching of each liquid body away from the double casing enveloping and dropping of each liquid body into a volume of air;

C3d) immersing of each droplet in a solution containing a reagent capable of reacting with the polyelectrolyte of the film in order to induce it to pass from a liquid state to a gelled state and form the gelled enveloping shell, the central kernel forming the core; and C3e) recovery of the colored particles formed.

Preferably, the first liquid solution is an aqueous composition comprising, or indeed even consisting of, the pigment(s), preferably obtained in the step a) or b), optionally a binder, in particular as defined here above, at least one preservative and at least one polymer, in particular selected from among hyaluronic acid or one of the salts thereof, carrageenan, gellan, a polysiloxane, and the mixtures thereof.

The first liquid solution preferably comprises more than 10% by weight, in particular more than 20% by weight, for example between 25 and 50% by weight of pigment(s) (cumulated content levels when there are a plurality of pigments). Such proportions are in effect adjusted so as to ensure that the mass proportion of pigment(s) in the colored particles obtained at the end of the method is greater than 3% by weight, preferably greater than 5% by weight.

The surfactant is in particular selected from among an anionic surfactant, a cationic surfactant, a non-ionic surfactant or mixtures thereof. Preferably, it is selected from among an alkyl sulphate, an alkyl sulphonate, an alkylarylsulphonate, an alkaline alkylphosphate, a dialkylsulphosuccinate, an alkaline earth salt of saturated or unsaturated fatty acids, an alkylpyridium halide salt or alkylammonium halide salt such as n-ethyldodecylammonium chloride or bromide, cetylammonium chloride or bromide, polyoxyethylenated and/or polyoxypropylenated derivatives of fatty alcohols, fatty acids or alkylphenols, or from arylphenols, alkyl glucosides, polysorbates, cocamides, or mixtures thereof. Preferably, it is sodium dodecyl sulfate.

The or each polyelectrolyte and the reagent capable of reacting with the polyelectrolyte are preferably as defined here above.

The second liquid solution containing a liquid polyelectrolyte capable of gelling may also contain a pearlescent pigment (nacre) and/or a dye, preferably of a colour different from that of the pigment of the first liquid solution.

For example, according to this second embodiment, the formulation described in step c) may be operationally implemented by following the method described in WO 2010/063937.

The core of the colored particles may comprise an intermediate droplet of an intermediate phase, the intermediate phase being placed in contact with the enveloping shell, and at least one, preferably one single, internal droplet of an internal phase being disposed in the intermediate droplet. The step c) then typically comprises the following sub-steps:

C4a) separated conveying in a triple casing enveloping (pipe-in-pipe) of an internal phase intended to form the one or more internal droplet(s) of the core, of an intermediate phase intended to form the intermediate droplet of the core, and a first solution containing a liquid polyelectrolyte capable of gelling intended for forming the gelled enveloping shell, the said first solution preferably containing a surfactant;

C4b) formation at the exit of the triple casing enveloping of a series of liquid bodies, each liquid body comprising at least one, preferably one single internal droplet of the internal phase disposed in an intermediate droplet of the intermediate phase, the said intermediate droplet being coated with a peripheral film formed of the first solution;

C4c) detaching of each liquid body away from the triple casing enveloping and dropping of each liquid body into a volume of air;

C4d) immersing of each liquid body in a solution containing a reagent capable of reacting with the polyelectrolyte of the film in order to induce it to pass from a liquid state to a gelled state and form the gelled enveloping shell;

C4e) recovery of the colored particles formed, preferably with a ratio of the volume of the core to the volume of the enveloping shell being greater than 2, advantageously less than 50, where the internal phase and/or the intermediate phase contains the pigment(s), preferably obtained in the step a) or b). Preferably, the internal phase is the one that contains the pigment(s). Preferably, the intermediate phase is the one that contains the pigment(s).

The polyelectrolyte, the surfactant and the reagent are preferably as defined here above.

The first solution containing a liquid polyelectrolyte capable of gelling intended for forming the gelled enveloping shell may in addition comprise a pearlescent pigment (nacres) and/or at least one dye, preferably of a color different from that of the pigment contained in the internal phase and/or the intermediate phase.

Generally, one of the phases from the internal phase and the intermediate phase is aqueous and the other is oily. For example, the intermediate phase is an aqueous composition comprising, or indeed even consisting of, the pigment(s), optionally a binder, in particular as defined here above, at least one preservative and at least one polymer, in particular selected from among hyaluronic acid or one of the salts thereof, carrageenan, gellan, a polysiloxane, and mixtures thereof, and the internal phase is a plant oil such as almond, apricot or jojoba oil.

The intermediate phase preferably comprises more than 10% by weight, in particular more than 20% by weight, for example between 25 and 50% by weight of pigment (cumulated content levels when there are a plurality of pigments). Such proportions are in effect adjusted so as to ensure that the mass proportion of pigment(s) in the colored particles obtained at the end of the method is greater than 3% by weight.

For example, the formulation described in step c) may be operationally implemented by following the method described in the patent application WO 2012/089820.

A solution comprising a milled and/or pretreated pigment as defined here above has a lower viscosity than a solution comprising an unmilled and untreated pigment. Generally, the viscosity:
  of the mixture obtained in the step C1a),
  of the mixture obtained in the step C2a),
  of the first liquid solution of step C3a),
  of the internal phase containing the pigment(s) of the step C4a) and/or of the intermediate phase containing the pigment(s) of the step C4b),
is in a range from 1 mPa·s to 500,000 mPa·s, preferably from 10 mPa·s to 300,000 mPa·s, more preferably from 400 mPa·s to 100,000 mPa·s, and more particular from 1,000 mPa·s to 30,000 mPa·s, as measured at 25° C. and at ambient pressure (1,013 mbar). The viscosity may be measured with a Brookfield apparatus model Viscometer LVDV2T at a speed of 10 revolutions per minute.

These viscosities can be adjusted by using a gelling agent, in particular as defined here above. For example:
  the mixture obtained in the step C1a),
  the mixture obtained in the step C2a),
  the first liquid solution of the step C3a),
  the internal phase containing the pigment(s) of the step C4a) and/or the intermediate phase containing the pigment(s) of the step C4b),
comprises a gelling agent, in particular as defined here above.

Regardless of the embodiment used, the method may comprise, after the step c), a step d) of rinsing of the colored particles.

In the case of complex capsules, the method may comprise, after step c), a step e) of depolymerisation. This step e) of depolymerisation serves the objective of removing the gelled enveloping shell when comprising at least one gelled polyelectrolyte. This step e) can be carried out by means of any depolymerisation method known to the person skilled in the art. In the case of an alginate based gelled enveloping shell, the depolymerisation may be carried out by immersion in a depolymerisation solution, such as, for example, a solution of sodium citrate concentrated at a mass content of at least 5%, typically of 10%. Mention may also be made of solutions of tartrate ions, phytic acid or EDTA, any solution of so-called chelating species for divalent cations, or even solutions of acrylic acid polymers of such types as carbomer, carbopol, polyacrylamide or polyacrylate.

Preferably, the intermediate phase (or enveloping shell) is not altered by the step e) of depolymerisation.

Advantageously, the method according to the invention does not include a step of drying the particles.

The invention also relates to a series of colored particles that can be obtained by the method mentioned above, the said particles comprising at least 3% by weight, preferably at least 5% by weight, in particular at least 10% by weight, in particular at least 13% by weight of pigment(s).

The invention also relates to the use of at least one series of colored particles for introduction into a cosmetic composition.

The particles or series of particles according to the invention can in particular be used in the cosmetics field.

The invention also relates to a cosmetic composition, preferably a make-up composition comprising at least one series of colored particles.

The cosmetic compositions according to the invention may comprise, in addition to the aforementioned ingredients, at least one physiologically acceptable medium.

The invention therefore also relates to a composition comprising at least one particle as defined here above or at least one series of particles as defined here above, in combination with an acceptable physiological medium.

The term "physiologically acceptable medium" is understood to refer to a medium which is particularly suitable for the application of a composition of the invention on to keratin materials, in particular the skin, the lips, the nails, the eyelashes or the eyebrows, and preferably the skin.

The physiologically acceptable medium is generally appropriately adapted to the nature of the support substrate to which the composition is to be applied, as well as to the overall appearance consistent with which the composition is to be packaged.

The presence of a physiologically acceptable medium can contribute to improving the storage/conservation and/or preserving the integrity over time of the colored particles according to the invention.

According to one embodiment, the physiologically acceptable medium is in the form of an aqueous gel, the viscosity of which is appropriate for ensuring the suspension of the colored particles according to the invention.

According to one embodiment, the cosmetic compositions are used for the purposes of make-up and/or care of keratin materials, in particular the skin.

The cosmetic compositions according to the invention may be personal care products, products for sun protection, cleansing (make-up removal), hygiene or make-up for the skin.

These compositions are therefore intended to be applied in particular on the skin, lips or hair.

Thus, the present invention also relates to the non-therapeutic cosmetic use of a cosmetic composition mentioned above, as a product for make-up, hygiene, cleansing, and/or care for keratinous materials, in particular the skin.

According to one embodiment, the compositions of the invention are in the form of a foundation, a makeup remover, a treatment/product for face and/or body and/or hair care, anti-aging, a sunscreen, an oily skin care, a whitening treatment, a moisturiser, a BB cream, tinted cream or make-up foundation, a face and/or body cleanser, a shower gel or a shampoo.

A care-treatment composition according to the invention may be in particular a sun protection composition, a skin care cream, a serum or deodorant.

The compositions according to the invention may be in various different forms, in particular in the form of a cream, balm, lotion, serum, gel, gel-cream or even mist.

In particular, a composition according to the invention is a care and/or make-up composition for keratinous substances, in particular the skin, and is in particular a make-up foundation composition.

In view of the foregoing, a composition according to the invention and in particular the particles according to the invention do not pertain to, and are therefore different from, "two-way cakes" or cosmetic compositions in the form of powders, as described in the document EP 1 036 555.

The present invention also relates to a non-therapeutic method for the cosmetic treatment of a keratinous material, in particular the skin, the lips or the hair, comprising at least one step of application on the said keratinous material of at least one composition according to the invention.

In particular, the present invention relates to a non-therapeutic treatment method for cosmetic treatment of the skin, lips or hair, comprising an application step of applying to the skin at least one composition according to the invention.

The cosmetic composition comprises preferably at least 3% by weight of pigment(s), in particular at least 5%, for example at least 7.5% by weight of pigment(s). The maximum mass proportion of pigment(s) in the composition is generally 50% or even 30%.

The coloration conferred by the colored particles may for example be measured by means of spectrocolorimetry and/or spectrophotocolorimetry.

More particularly, the cosmetic composition may for example be mascara, a product for skin tone/complexion enhancement, such as a make-up foundation, a liner ("eyeliner"), an eyeshadow or blush, a product for the lips such as a lipstick or a lip gloss, soap possibly in liquid form, shampoo, conditioner, nail polish, preferably eye shadow, complexion care products or lip care products. The cosmetic composition may be in the form of a monophasic or biphasic lotion, a water-in-oil or oil-in-water emulsion, a gel, a stick or a cream.

The make-up composition preferably has a coverage greater than or equal to 10, in particular greater than or equal to 15, or indeed preferably even greater than or equal to 40, preferably greater than or equal to about 45, in particular greater than or equal to about 50, notably greater than or equal to about 60, more particularly greater than or equal to about 80, in particular ranging from 90 to 100, or indeed even about 100. The coverage corresponds to the capacity or ability of the make-up composition to "mask the skin"/to "conceal imperfections".

The coverage of the compositions is measured at a finite thickness of 50 μm at 25° C., for the liquid compositions, to be applied to the lips, in particular liquid lipsticks, liquid lip glosses and liquid lip balms, and at a thickness of 150 μm for eye shadows, liquid make-up foundations, mascaras and other liquid make-up products not intended to be applied to the lips. The composition is spread over matte black and matte white contrast cards, for example of the brand LENETA Form WPI for the matte black card and Leneta IA for the matte white card. The application can be performed with an automatic spreader. The measurements are carried out on the compositions thus spread. Reflectance spectra are acquired by using a MINOLTA 3700-d spectrocolorimeter (diffuse measurement geometry and D65/10° observation, excluding specular component mode, small aperture (CRE-ISS)) on the black and white backgrounds. The spectra are expressed in colorimetric coordinates in the CIELab76 space pursuant to the provisions of the International Commission on Illumination in accordance with the Recommendation 15: 2004. The contrast ratio, or coverage, is calculated by deriving the arithmetic mean of Y on a black background, divided by the mean value of Y on a white background, multiplied by 100.

The expressions "comprised between . . . and . . . ", "in a range from . . . to . . . " and "from . . . to . . . " are to be understood as being inclusive of limits, unless otherwise specified.

The examples that follow illustrate the present invention without intending to limit the scope thereof.

Example 1: Impact of Treating a Pigment with an Additive that Improves Dispersibility Thereof and of Grinding on the Quality of Pigment Dispersion Various pigment dispersions (white, black, yellow and red pigments) in glycerin were prepared with the compositions indicated in Table 1. The additive used to improve the dispersibility of the pigments in the aqueous phase is phytic acid.

Preparation of a Dispersion 1 of Treated and Unmilled Pigments

A dispersion of white, black, yellow and red pigments treated with phytic acid on the surface in glycerin was prepared with a proportion by weight of pigments/glycerin of 1/1 by following the compositions shown in Table 1.

TABLE 1

Composition of pigment dispersion comprising treated pigments

| Ingredient | Nature (INCI) | Supplier | Mass (g) |
|---|---|---|---|
| Phytic Acid treated White Pigment | CI77891 (and) Phytic Acid (and) Sodium Hydroxide | Sensient Cosmetic Technologies | 41.5 |
| Phytic Acid treated Yellow Pigment | CI77492 (and)) Phytic Acid (and) Sodium Hydroxide | Sensant Cosmetic Technologies | 5.5 |
| Phytic Acid treated Black Pigment | CI77499 (and) Phytic Acid (and) Sodium Hydroxide | Sensient Cosmetic Technologies | 0.6 |
| Phytic Acid treated Red Pigment | CI77491 (and) Phytic Acid (and) Sodium Hydroxide | Sensient Cosmetic Technologies | 2.4 |
| Glycerin | — | | 50.0 |

Under agitation with use of a propeller (Ika), the pigments were incorporated into the glycerin. The agitation was maintained for a period of 30 minutes at 600 revolutions per minute.

The pigment dispersion obtained was smooth, glossy, fluid. Its viscosity at 25° C. was 7.32 Pa·s at a speed of 10 revolutions per minute and at module 4, for 30 s, torque 12.2.

The dispersion was placed between two glass plates. The points were then visible. The colour develops between the glass plates.

Preparation of a Dispersion 2 of Treated and Ground (Milled) Pigments

The composition of pigment dispersion is also identical as in Table 1.

The following protocol was adhered to: In a beaker, under agitation with use of a propeller at 600 revolutions per minute for a period of 30 minutes, the treated pigments were progressively incorporated into the glycerin. The mixture was then ground (milled) on a three-roll mill (EXAKT 50i) with three consecutive passes through the mill. This grinding corresponds to the step b) defined in the application.

The pigment dispersion obtained was smooth, glossy, fluid. Its viscosity at 25° C. was 5.46 Pa·s at a speed of 10 revolutions per minute and at module 4, for 30 s, torque 2.9.

It was placed between two glass plates and appeared homogeneous, without clumps/pigment agglomerate/color dots. The color remained stable.

Preparation of a Dispersion 3 of Untreated Unmilled Pigments

A dispersion of untreated white, black, yellow and red pigments in glycerin was prepared with a proportion by weight ratio of pigments/glycerin of 1/1 according to the compositions indicated in Table 2.

TABLE 2

Composition of pigment dispersion comprising untreated pigments

| Component | Nature (INCI) | Supplier | Mass (g) |
| --- | --- | --- | --- |
| White Pigment | CI77891 | Sensient Cosmetic Technologies | 41.5 |
| Yellow Pigment | CI77492 | Sensient Cosmetic Technologies | 5.5 |
| Pigment Black | CI77499 | Sensient Cosmetic Technologies | 0.6 |
| Pigment | CI77491 | Sensient Cosmetic Technologies | 2.4 |
| Glycerin | — | | 50.0 |

Under agitation with use of a propeller (Ika), the pigments were incorporated into the glycerin. The agitation was maintained for a period of 30 minutes at 600 revolutions per minute. The pigment dispersion obtained was smooth, glossy, thick. Its viscosity at 25° C. at a speed of 10 revolutions per minute and at module 4 for 30 seconds, was too great to be measured with the aforementioned device.

It was placed between two glass plates. White, black and red dots were observed. The colour develops between the glass plates.

Preparation of a Dispersion 4 of Untreated and Ground (Milled) Pigments

The composition of pigment dispersion is also identical as in Table 2.

The following protocol was adhered to: In a beaker, under agitation with use of a propeller at 600 revolutions per minute for a period of 30 minutes, the untreated pigments were progressively incorporated into the glycerin. The mixture was then ground (milled) on a three-roll mill (EXAKT 50i) with three consecutive passes through the mill. This grinding corresponds to the step b) defined in the application.

The viscosity of the dispersion obtained at 25° C. at a speed of 10 revolutions per minute and at module 4 for 30 seconds was too great to be measured with the aforementioned device.

Viscosity of the dispersions and distributions of size of particles of the pigments are provided in Table 3 here below.

TABLE 3

Viscosities of the dispersions and the particle size distributions of pigments

| Dispersion | | D10 (μm) | D50 (μm) | D90 (μm) | Viscosity |
| --- | --- | --- | --- | --- | --- |
| 3 | Untreated unmilled pigments | 3.19 | 5.09 | 7.89 | Too thick- cannot be measured |
| 4 | Untreated milled pigments | 2.69 | 4.10 | 5.91 | Too thick- cannot be measured |
| 1 | Phytic acid treated Unmilled pigments | 0.32 | 0.47 | 1.01 | 7.32 Pa, s |
| 2 | Phytic acid treated milled pigments | 0.42 | 1.49 | 0.68 | 5.46 Pa, s |

The particle size (granulometry) was measured by laser diffraction by using a HORIBA LA-960S model particle size analyzer (granulometer).

These examples show that the treatment of the pigment with phytic acid and grinding (milling) makes it possible to fluidify the pigment dispersion and to improve the dispersion of the pigment in the dispersion. The most satisfactory dispersion is the one obtained from phytic acid treated and ground (milled) pigments. The higher the quality of the dispersion, the greater the likelihood of the particles prepared from the dispersion having a high pigment content.

Example 2: Preparation of Colored (Dyed) Particles Comprising a Liquid Core and a Gelled Alginate Based Enveloping Shell White, yellow, black and red pigments pretreated with phytic acid were used to prepare colored (dyed) particles with a high pigment content.

Preparation of a Pigment Dispersion

A dispersion of white, black, yellow and red pigments surface treated with phytic acid in glycerin was prepared with a proportion by weight ratio of pigments/glycerin of 1:1 according to the compositions indicated in Table 1 of Example 1.

The composition of pigment dispersion is also identical as in the said Table 1.

The following protocol was adhered to: In a beaker, under agitation with use of a propeller at 500 revolutions per minute for 1 min, the treated pigments were progressively incorporated into 30 g of glycerin. The mixture was very viscous.

It was then ground (milled) on a three-roll mill (EXAKT 50i) with three consecutive passes through the mill. This grinding corresponds to the step b) defined in the application. The mill was then cleaned with the remaining 20 g of glycerin to obtain the treated pigments in glycerin. The particle size measured by laser diffraction using a HORIBA LA-960S granulometer was D10: 0.42—D50: 1.49—D90: 0.68.

The pigment dispersion obtained was smooth, glossy, very viscous. Its viscosity at 25° C. was 5.46 Pa·s at a speed of 10 revolutions per minute and at module 4, for 30 s, torque 13.3.

The colored particles were then formulated using a millifluidic method similar to that described in the application WO 2010/063937, in particular from a solution comprising the glycerin (used as a binder during grinding), the pretreated milled pigments obtained above, preservatives and a hyaluronic acid gel.

Preparation of a Hyaluronic Acid Gel

A hyaluronic acid gel having the composition specified in Table 4 was prepared.

TABLE 4

Composition of hyaluronic acid gel

| Component | Supplier | Mass (g) |
| --- | --- | --- |
| Phenoxyethanol (preservative) | Thor | 0.8 |
| Pentylene glycol (preservative) | Symrise | 0.2 |
| Hyaluronic acid | Lehvoss | 0.95 |
| Distilled water | — | 96.25 |

The following protocol was adhered to: In a beaker, the distilled water and preservatives were mixed. The hyaluronic acid was then progressively incorporated in a fine drizzle under agitation with use of a propeller (Ika Eurostar 60 apparatus). The agitation was maintained until a transparent, homogeneous gel was obtained. Its viscosity at 25° C. was 2.1 Pa·s at a speed of 10 revolutions per minute and at module 4, for 30 s, torque 3.5, measured with a Brookfield model Viscosimeter LVDV2T apparatus.

Incorporation of the Pigment Dispersion into the Hyaluronic Acid Gel

TABLE 5

Composition of the hyaluronic acid gel comprising the pigment dispersion.

| Component | Expl 1 | Expl 2 | Expl 3 | Expl 4 | Expl 5 |
|---|---|---|---|---|---|
| Mass of hyaluronic acid gel (g) | 4 | 2 | 3 | 1 | 0.5 |
| Mass of pigment dispersion (g) | 6 | 8 | 7 | 9 | 9 |
| Distilled water (mL) | — | — | — | — | 0.5 |
| Mass content of pigment in relation to hyaluronic acid gel | 30% | 40% | 35% | 45% | 45% |
| Viscosity (Pa · s) (Module 4, speed: 10 revolutions per minute, 30 s Temperature: 25° C.) | 2.40 (torque 4.0) | 2.64 (torque 4.4) | 2.46 (torque 4.1) | 3.24 (torque 5.4) | 1.74 (torque 2.9) |

Preparation of Colored (Dyed) Particles by Implementing Steps C3a) to C3e).

A mixture (=mixture A) of 54% by weight of pigmented hyaluronic acid gel obtained and 46% by weight of unpigmented hyaluronic acid gel having the composition indicated in Table 4, was used as the first liquid solution in the method described in the application WO 2010/063937.

The method for preparing capsules is based on (i) a millifluidic method similar to that described in the application WO 2010/063937 and thus (ii) on the implementation of the following three solutions:
- mixture A as the first liquid solution intended for forming the core of the particles,
- an aqueous solution containing 3% by weight of sodium alginate as the second liquid solution intended to form the gelled enveloping shell of the particles, and
- a third solution featuring a calcium bath dedicated to gelling the second solution and thus enabling the formation of the gelled enveloping shell of the particles.

Composition of the Calcium Bath

| Name | Supplier | INCI name | % w/w |
|---|---|---|---|
| Reverse osmosis water | / | Aqua | qsp |
| Calcium chloride | | Calcium chloride | 20.00 |
| Tween 20 | | Polysorbate 20 | 0.10 |
| | TOTAL | | 100.00 |

The flow rates considered at the level of the millifluidic device are:

| Solution | Flow rate (in ml/h) |
|---|---|
| first solution | 17.5 |
| second solution | 5 |

According to one particular embodiment, the particles may then be stored/conserved in a physiologically acceptable medium, in particular an aqueous gel suspension as described here below.

| Physiologically acceptable medium | | | % |
|---|---|---|---|
| Name | Supplier | INCI Name | w/w |
| Reverse osmosis water | / | Aqua | qsp |
| MICROCARE PE | Thor | PHENOXYETHANOL, AQUA | 0.5 |
| MICROCARE EMOLLIENT PTG | Thor | PENTYLENE GLYCOL, AQUA | 3.00 |
| GLYCERINE CODEX | Interchimie | GLYCERIN, AQUA | 6.00 |
| ZEMEA PROPANEDIOL | Dupont Tate & Lyle | PROPANEDIOL, AQUA | 4.00 |
| RHODICARE T | Rhodia | XANTHAN GUM, AQUA | 0.46 |
| HEPES-LUV | Hopax | HYDROXYETHYL-PIPERAZINE ETHANE SULFONIC ACID, AQUA | 0.50 |
| SODIUM HYDROXIDE PELLETS PRS CODEX | Panréac | SODIUM HYDROXIDE | 0.03 |
| | Total | | 100.00 |

TABLE 6 mass proportion of pigment in the colored particles obtained

| Phase used | Expl 1 | Expl 2 | Expl 3 | Expl 4 | Expl 5 |
|---|---|---|---|---|---|
| mass proportion of pigment in the colored particles obtained at the end of step c) | 13.8% | 18.4% | 16.1% | 20.7% | 20.7% |

The colored particles obtained included very large mass proportions of pigments (between 13 and 21% by mass of pigment), which makes them particularly suitable for being introduced into make-up compositions, and in particular in make-up foundations.

Preparation of a Make-Up Composition

Make-up compositions comprising 55% by weight of colored particles obtained were prepared.

TABLE 7

Mass proportion of pigment in make-up compositions prepared

| Phase used | Expl 1 | Expl 2 | Expl 3 | Expl 4 | Expl 5 |
|---|---|---|---|---|---|
| mass proportion of pigment in make-up composition prepared | 7.59% | 10.12% | 8.8% | 11.39% | 11.39% |

The compositions advantageously have a high pigment content, which makes them very suitable for make-up applications, and most particularly for make-up foundations.

What is claimed is:

1. A particle comprising at least 3% by weight of pigment(s), in relation to the weight of said particle, wherein said particle comprises a core that is liquid, or at least partially gelled or at least partially thixotropic, and an enveloping shell which totally encapsulates said core, said core being monophasic or comprising an intermediate droplet of an intermediate phase, the intermediate phase being placed in contact with the enveloping shell, and at least one internal droplet of an internal phase being disposed in the intermediate droplet, and wherein the diameter of said particle is in a range from 0.1 mm to 10 mm.

2. The particle according to claim 1, selected from solid particles or particles of the core/shell type.

3. A series of particles, in which at least one particle comprises at least 3% by weight of pigment(s), in relation to the weight of said particle, wherein said one particle comprises a core that is liquid, or at least partially gelled or at least partially thixotropic, and an enveloping shell which totally encapsulates said core, said core being monophasic or comprising an intermediate droplet of an intermediate phase, the intermediate phase being placed in contact with the enveloping shell, and at least one internal droplet of an internal phase being disposed in the intermediate droplet, and wherein the diameter of said particles is in a range from 0.1 mm to 10 mm.

4. The series of particles according to claim 3, in which the coefficient of variation of the diameters of the colored particles is less than 10%.

5. The series of particles according to claim 4, in which the said particles are solid particles or core/shell type particles.

6. The series of particles according to claim 3, in which the said particles further comprise at least one gelling agent.

7. The series of particles according to claim 3, in which the said particles further comprise at least one smoothening-concealing effect filler.

8. The series of particles according to claim 3, in which the said particles further comprise at least one coloring agent that is different from the said one or more pigment(s).

9. A composition comprising at least one particle according to claim 1 or comprising a series of particles according to claim 3.

10. A cosmetic composition, comprising at least one particle according to claim 1 or comprising a series of particles according to claim 3, in combination with a physiologically acceptable medium.

11. The composition according to claim 9, the said composition being a make-up composition.

12. A non-therapeutic method for the cosmetic treatment of a keratinous material, comprising at least one step of application on the said keratinous material of at least one composition according to claim 9.

13. The particle according to claim 1, wherein the core comprises an intermediate droplet of an intermediate phase, the intermediate phase being placed in contact with the enveloping shell, and at least one internal droplet of an internal phase being disposed in the intermediate droplet.

14. The particle according to claim 1, comprising at least 10% by weight of pigment(s), in relation to the weight of the said particle.

* * * * *